Figure 1:
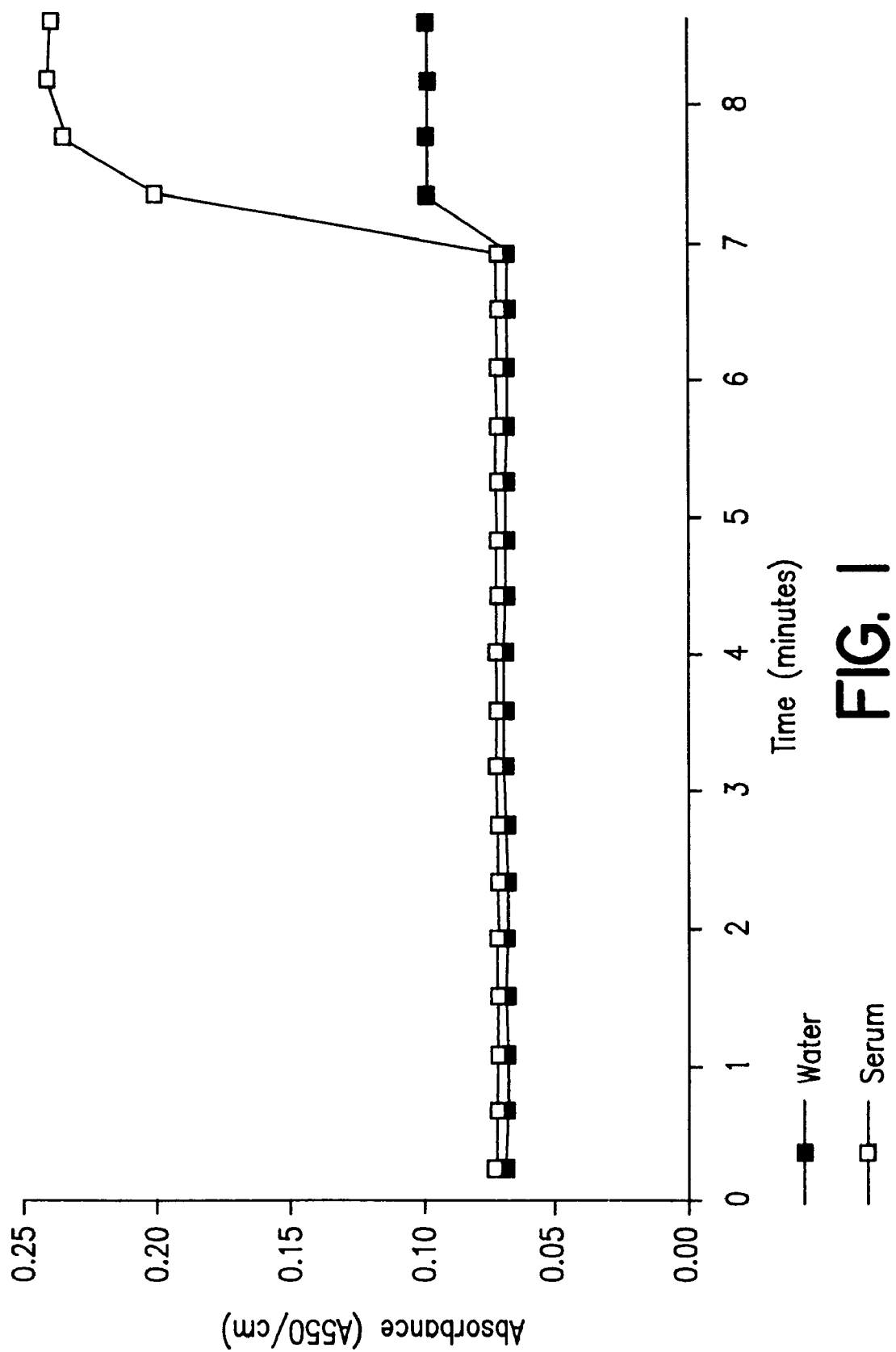

United States Patent [19]
Torrens et al.

[11] Patent Number: 6,008,006
[45] Date of Patent: Dec. 28, 1999

[54] DETERMINATION OF GLYCATED PROTEINS

[75] Inventors: David John Torrens; Darren Paul Shipley; Sarah Catherine Poller, all of Maidstone, United Kingdom

[73] Assignee: Genzyme Limited et al., United Kingdom

[21] Appl. No.: 08/945,724

[22] PCT Filed: May 3, 1996

[86] PCT No.: PCT/EP96/01912

§ 371 Date: Nov. 5, 1997

§ 102(e) Date: Nov. 5, 1997

[87] PCT Pub. No.: WO96/34977

PCT Pub. Date: Nov. 7, 1996

[30] Foreign Application Priority Data

May 5, 1995 [GB] United Kingdom .................... 9509248
Aug. 16, 1995 [GB] United Kingdom .................... 9516757

[51] Int. Cl.⁶ ................................ C12N 9/00; C12Q 1/37

[52] U.S. Cl. .................................. 435/23; 435/25; 435/28; 435/189; 435/190; 435/192; 435/219

[58] Field of Search .................................. 435/23, 28, 25, 435/219, 192, 189, 190

[56] References Cited

U.S. PATENT DOCUMENTS 5,370,990   12/1994   Staniford et al. .

FOREIGN PATENT DOCUMENTS

0526150 A1   2/1993   European Pat. Off. .

*Primary Examiner*—Leon B. Lankford, Jr.
*Attorney, Agent, or Firm*—F. Brad Salcedo

[57] ABSTRACT

The amount of glycated proteins in a sample can be quantified by reacting the sample with first a reagent which is a combination of a protease and a peroxidase and second with a ketoamine oxidase. A kit which contains the combined peroxidase/protease enzyme reagent and also the ketoamine oxidase is also disclosed.

10 Claims, 5 Drawing Sheets

DETERMINATION OF GLYCATED PROTEINS

This invention relates to the determination of glycated proteins; more particularly, it relates to such a method involving the use of a proteinase in the same reagent as a peroxidase and to a kit therefor.

Horseradish peroxidase is an oxidoreductase (donor:hydrogen peroxide oxidoreductase; EC 1.11.1.7). It is widely used in the life sciences as an indicator enzyme (see, for example, Essays in Biochemistry, 1994; 28: 129–146), and is one of a family of peroxidase enzymes. The particularly useful features of this enzyme are its ease of coupling to carriers, such as antibodies or other enzymes, its high rate of activity with a range of substrates and good thermal stability. It consists of a single polypeptide comprising 308 amino acids and has a relative molecular mass of 44,000, which incorporates a haemin prosthetic group giving it a brown colouration. The enzyme has four disulphide bridges and contains two calcium ions, removal of which leads to a reduction in stability.

This enzyme catalyses the transfer of hydrogen from a hydrogen donor to a hydrogen acceptor. The hydrogen acceptor is usually hydrogen peroxide, although methyl and ethyl peroxides may also be used. Hydrogen peroxide is reduced according to the following reaction:

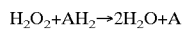

$$H_2O_2 + AH_2 \rightarrow 2H_2O + A$$

A wide range of hydrogen donors may be used. These include phenols, aminophenols, indophenols, diamines and leuco dyes. The oxidative process of hydrogen removal from such compounds generates products which may be detected visually or quantified, usually in a spectrophotometer. Other means of detection used have included fluorimetry, luminometry and electrochemistry.

The enzyme may be physically coupled to other proteins, such as antibodies or fragments thereof. This allows the specific binding properties of the antibody to be used to measure an analyte or to identify histologically the location of an antigen. It may also be chemically linked to an oxidase enzyme to quantify the substrate of the oxidase. There are many analytes that may be measured using specific oxidases. Of these, several are present in biological fluids where analysis thereof may be clinically helpful. The use of phenol and aminoantipyrene as chromogens linked to an oxidase— peroxidase system has long been known (see, for example, Ann Clin Biochem, 1969, 6: 24–27). More recently, alternatives to phenol, such as N-ethyl-N-(2-hydroxy-3-sulphopropyl)-m-toluidine (TOOS), have been proposed which are more sensitive and are coloured over a wide pH range (see, for example, Chem Pharm Bull., 1982; 30: 2492–2497).

One such analyte is glycated protein, or fructosamine. This is the product of a non-enzymatic reaction by which glucose or other sugars may form condensation products with free amine groups of protein (see, for example, Clin Chem, 1987; 33: 2153–2163. In the blood, the main proteins that are glycated are albumin, in which exposed lysine residues provide the free amine group, and haemoglobin, in which the N-terminal valine amino acid may also react with glucose. In diabetic subjects, the concentrations of the protein components of blood vary between fairly narrow limits. In contrast, the glucose concentration may change significantly in a short period of time. Many of the pathological changes experienced by diabetic patients are the consequence of prolonged exposure of proteins to elevated glucose concentrations. Therefore, the measurement of glycated protein is clinically useful in assessing the average glucose exposure over the lifetime of the protein.

Several methods have been used to measure total glycated protein. The current reference method is the furosine procedure (see, for example, J Clin Chem Clin Biochem, 1981; 19: 81–87). This involves protein digestion in 6 molar hydrochloric acid at 95–100° C. for 18 hours. Furosine is a product of glycated lysine under these conditions and may be measured by HPLC. This method is too complex and time-consuming for routine use. The thiobarbituric acid procedure is slightly simpler as it uses a shorter acid digestion (2–5 hours) yielding 5-hydroxymethylfurfuraldehyde, which may be reacted with thiobarbituric acid to give a derivative having an absorbance maximum at 443 nm. Another method is phenylboronate affinity chromatography. Under alkaline conditions, phenylboronate complexes with the cis-diol groups of sugars. However, even with close temperature control and prior removal of glucose, the precision of this method is poor.

The simplest commercially available and most widely used method for determining serum glycated protein is based on the ability of fructosamines in alkaline solution to reduce nitroblue tetrazolium (NBT) to produce a blue dye (see, for example, Clin Chem Acta, 1982; 127: 87–95). The great advantage of this procedure is its ease of automation. It has since been reformulated to reduce interference due to protein concentration, lipids and uric acid (see, for example, Clin Chem, 1991; 37: 552–556). However, only about half of the measured reducing activity in normal or well-controlled diabetics is due to glycated protein (see, for example, Clin Chem, 1988; 34: 320–323).

To avoid problems of poor specificity seen with the NBT method, an enzymatic method has been developed (see, for example EP-A-526 150). This two reagent system uses a proteinase to degrade serum protein, followed by the use of a ketoamine oxidase which acts on the glycated fragments. The oxidase may be linked to a peroxidase and chromogen system in an endpoint determination in which the amount of colour formed is proportional to the quantity of glycated protein in the sample. A similar process using an enzyme from a different source has also been described (see, for example, EP-A-576 838). However, these methods are likely to suffer significant interference from ascorbate and bilirubin when used with fresh samples. They also use peroxidase in a second reagent and require a reagent blank correction.

There may also be mentioned EP-A-678576, which relates to a fructosyl amino acid oxidase produced by culturing a strain of Fusarium or Gibberella.

The proteinase in the first reagent must show high activity towards the glycated protein and the ability to release the substrate for the ketoamine oxidase. The ability to cleave different peptide bonds is advantageous for the rapid release of the substrate. Several proteinases which are non-specific, such as pronase and proteinase K, are known, together with many other classes of proteinase having different specificities from a wide variety of species, which may be used alone or in combination.

Because of the requirement for an extensive proteolysis of blood proteins, and the non-specific nature of the proteinase, the retention of an enzyme activity in the same solution as the proteinase is most unlikely. Therefore, the peroxidase would have to be included in the second of the two reagents, so that the only exposure of peroxidase to the proteinase would be for a relatively short time in the cuvette after the second reagent addition. The absorbance of the cuvette is measured just before the addition of the second reagent and again after the ketoamine oxidase/peroxidase system has produced the colour. The change in the absorbance between these two readings from a sample is due not only to the amount of glycated protein present in the sample, but also to the absorbance of the second reagent itself. Therefore a blank sample must be analysed so that a correction may be made.

For widespread acceptance of a clinical method, it is important that interference from substrates other than the desired analyte be minimised. Two compounds known to interfere with oxidase-peroxidase systems are bilirubin and ascorbate (see, for example, Ann Clin Biochem, 1984; 21: 398–404). The concentration of glycated protein in normal serum is about 0.1 mmol/L. The interference is more serious with analytes present at relatively low concentration rather than analytes, such as glucose or cholesterol, with normal concentrations in excess of 3 mmol/L. A high oral dose of vitamin C may cause serious interference even with a cholesterol assay (see, for example, Clin Chem, 1992; 38: 2160).

Different approaches have been used to reduce bilirubin interference. These include reduction of the reaction pH to 6.1 (see, for example, Clin Chem, 1981; 27: 375–379). This is not suitable for an enzymatic glycated protein method as the necessary enzymes require a higher pH. Alternatively, samples may be pretreated with peroxidase and hydrogen peroxide, which oxidises bilirubin (see, for example, Clin Chem, 1992; 38: 2411–2413). However, this is not suitable as it involves an extra reagent and would be likely to interfere with the subsequent oxidase reaction. Bilirubin oxidase has also been used to remove bilirubin (see, for example, Clin Chem, 1984; 30: 1389–1392), but an extra reagent would be required as the bilirubin oxidase is unlikely to retain its activity in the presence of the proteinase in the first reagent of the glycated protein assay.

Potassium ferrocyanide has been used to remove bilirubin interference up to 170 $\mu$mol/L in an assay for uric acid (see, for example, Clin Chem, 1980; 26: 227–231). Others have shown greater removal of interference, but the incorporation of potassium ferrocyanide into the first reagent of a two reagent system caused poor reagent stability (see, for example, Clin Chem, 1993; 31: 861–868). As will be described below, it has now been found that bilirubin interference up to 400 $\mu$mol/L may be removed by potassium ferrocyanide added to the first reagent of a two reagent assay for glycated protein and that the liquid reagent is stable for several weeks at 4° C.

Several methods have been used to protect oxidase/peroxidase systems from interference by ascorbate. The most commonly used means is ascorbate oxidase (see, for example, Clin Chem, 1980; 26: 227–231), which is not suitable for inclusion in a reagent containing proteinase as it is rapidly broken down. Prior treatment with activated charcoal (see, for example, Clin Chem, 1989; 35: 2330–2333) is inconvenient.

Removal of ascorbate interference by metals having a redox potential equal to or above that of ascorbate, but below the redox potential of a chromogenic substance has been described. Such metals, including copper, might be found in Groups VIII, I-B, II-B and IV-A of the Periodic Table (see, for example, U.S. Pat. No. 3,411,887). It is important that the redox potential of the metal ion is below that of the chromogenic substance, otherwise the metal ion itself would generate colour in the absence of the intended analyte. Another report tested copper in a similar oxidase/peroxidase system, but found that only small effects were seen even with copper concentrations as high as 30 mmol/L (see, for example, Clin Chem, 1982; 28: 578–588).

Surprisingly, in accordance with the present invention as will be described below it is possible to remove ascorbate interference in an oxidase/peroxidase method for measuring glycated protein using copper at concentrations below 0.1 mmol/L. Furthermore, in this system, if water is used as a sample rather than serum or plasma, copper is capable of directly oxidising the chromogen system. Therefore, the redox potential of the copper must be higher than that of the chromogen system. The reason why copper does not interfere in the analysis of serum or plasma samples may be due to the binding of copper by the products of proteinase digestion of the blood proteins.

An object of the present invention is to provide an enzymatic method for the determination of glycated protein in biological materials in which the peroxidase is formulated in the same reagent as the proteinase. Surprisingly, peroxidase activity is not affected by the proteinase. Other components of the second reagent do not contribute significantly to the cuvette absorbance, so corrections using a blank sample are not required. The absorbance change may simply be compared to that seen with a calibrant containing a defined amount of glycated protein.

A further object of the present invention is to protect the measurement of glycated protein from interference due to ascorbate or bilirubin which may be present in the sample. The satisfactory removal of ascorbate interference may also depend on the inclusion of peroxidase in the first rather than the second reagent.

The present invention may also be generally applicable to a variety of processes requiring a peroxidase where it would be advantageous to mix it with a proteinase. Other applications would include cases where an analyte has to be removed from protein to allow its measurement by an oxidase, or where intact proteins interfere with a method. The present method would also be suitable for determining specific glycated components in biological fluids and for measuring glycated haemoglobin.

The present invention provides a method for the determination of a glycated protein in a sample characterised in that it comprises: mixing the sample and a first reagent containing a proteinase and a peroxidase so as to produce a substrate capable of oxidation by a ketoamine oxidase; adding a second reagent containing a ketoamine oxidase; and measuring hydrogen peroxide produced or oxygen consumed so as to detect and/or quantify the glycated protein.

The present invention also provides a kit for the determination of a glycated protein characterised in that it comprises: a first reagent containing a proteinase and a peroxidase; a second reagent containing a ketoamine oxidase; and, optionally, means for measuring hydrogen peroxide produced or oxygen consumed.

Typically, the present methodology is applied to biological samples comprising a body fluid, such as blood serum or plasma.

In accordance with the present invention, the proteinase is generally proteinase K, preferably from *Tritirachium album*, and the peroxidase is horseradish peroxidase. Preferably, the ketoamine oxidase is obtainable from the bacterial group Klebsiella, from the fungal genera Fusarium or Acremonium or from the yeast genus Debaryomyces, preferably from Fusarium. (A ketoamine oxidase catalyses the oxidation of the carbon atom in position 1 of a sugar moiety of a glycated protein with consequent hydrolytic disruption of an amine bond to release a sugar osone and hydrogen peroxide from an amino acid.)

Commonly, the required measurement involves the use of an optionally modified Trinder reaction (sometimes termed a "PAP" method) or an oxygen electrode.

In preferred embodiments of the present invention, ascorbate interference is countered by the inclusion in the first reagent of a copper (II) compound, preferably copper (II) acetate, and optionally cholic acid and/or bathophenanthroline disulphonic acid; and/or bilirubin interference is countered by the inclusion in the first and/or the second reagent of a ferrocyanide salt, preferably potassium ferrocyanide. Furthermore, there may be included in the second reagent ethylene diamine tetraacetic acid and/or mannitol with a view to maintaining ketoamine oxidase activity.

A presently-preferred embodiment of the present invention uses proteinase K from *Tritirachium album* at a concentration of from 1 to 10 g/L in the cuvette, together with horseradish peroxidase at a cuvette concentration of from 0.01 to 1 g/L.

The present invention will be further illustrated by the following Examples:

EXAMPLE 1

Two pairs of reagents were prepared for the measurement of glycated protein. One pair contained peroxidase in the first reagent, together with the proteinase, and the other pair contained peroxidase in the second reagent. The first pair contained 12 g/L proteinase K, 0.4 g/L horseradish peroxidase and 3.0 mmol/L 4-aminoantipyrene in 100 mmol/L of (N-2-hydroxyethyl)piperazine-N'-(3-propanesulphonic acid) (EPPS) buffer pH 8.5 in the first reagent, and 10000 U/L ketoamine oxidase and 26.6 mmol/L TOOS in 100 mmol/L EPPS buffer, pH 8.5, in the second reagent. The second pair contained 12 g/L proteinase K and 3.0 mmol/L 4-aminoantipyrene in 100 mmol/L EPPS buffer, pH 8.5, in the first reagent, and 10000 U/L, ketoamine oxidase, 1.33 g/L horseradish peroxidase and 26.6 mmol/L TOOS in 100 mmol/L EPPS buffer, pH 8.5, in the second reagent.

The reagents were tested using a Cobas Mira S autoanalyser. 100 µL of the reagent containing the proteinase was mixed in a plastic cuvette with 10 µ/L of diabetic human serum and 40 µL of water diluent to wash the inside of the sample probe. After a 7 minute incubation at 37° C., 30 µL of the second reagent and 20 µL of water diluent were mixed into the same cuvette. The cuvette absorbance was measured at 550 nm at 25 second intervals from the start of the procedure until 1.5 minutes after the addition of the second reagent. The analyser automatically corrects the absorbance results to account for the dilution of the cuvette contents as the second reagent is added.

The results from the formulation in which peroxidase was protected from the proteinase by its addition in the second reagent are illustrated in accompanying FIG. 1. To calculate the absorbance change that is due to glycated protein in the serum sample, the absorbance change of the water sample due to the colour of the added peroxidase must first be subtracted.

Figure 2:
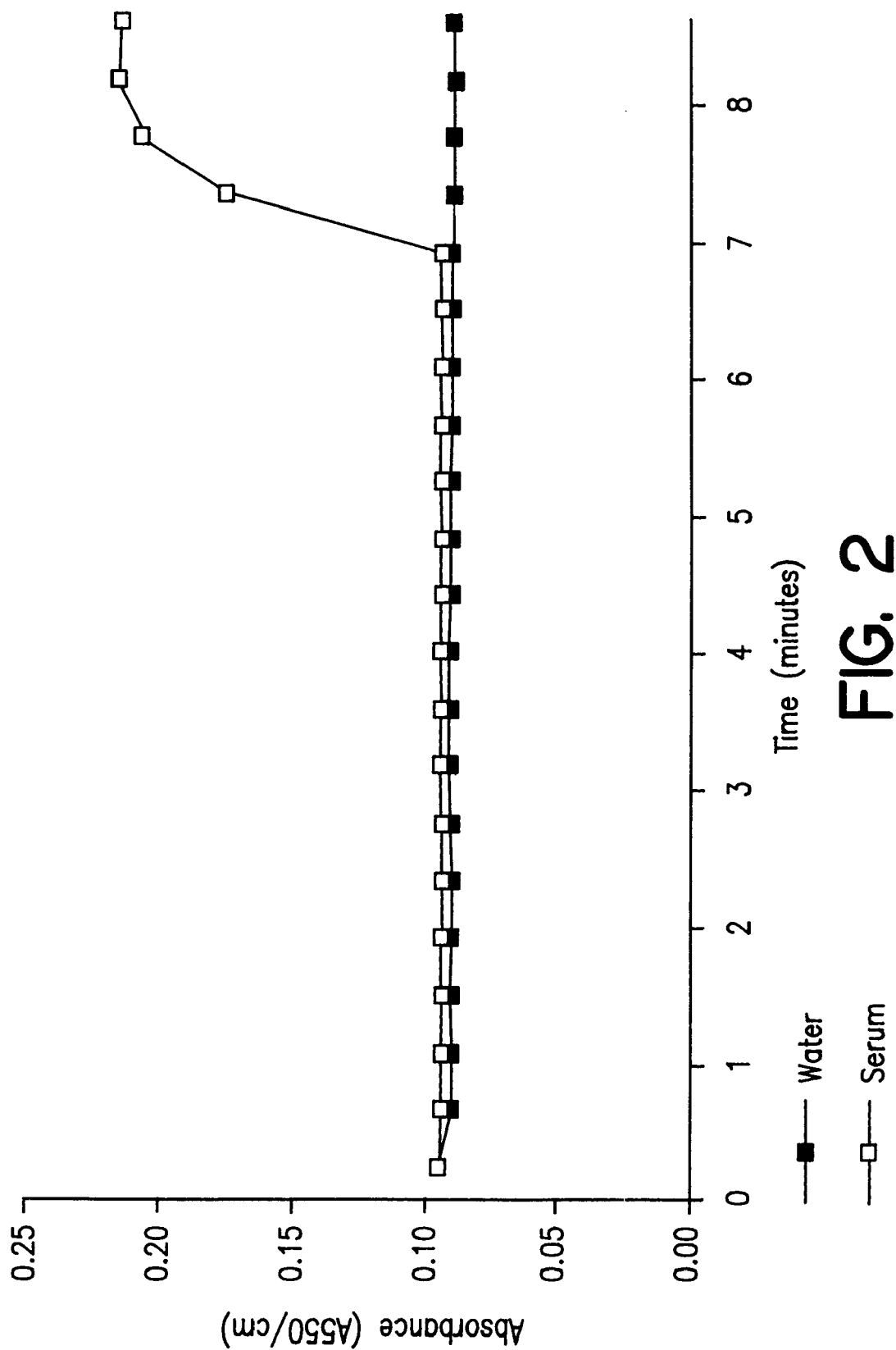

Accompanying FIG. 2 illustrates the results from the formulation in which the peroxidase was added as part of the first reagent. The water sample shows no increase in absorbance on the addition of the second reagent. Despite the presence of the proteinase with the peroxidase, the absorbance change seen with the serum sample is the same as the water blank subtracted data of accompanying FIG. 1.

EXAMPLE 2

A reagent was prepared containing 0.2 g/L horseradish peroxidase and 2.25 mmol/L 4-aminoantipyrene in 100 mmol/L EPPS buffer, pH 8.5, with and without 12 g/L proteinase K. The reagents were stored at room temperature. Peroxidase activity was measured in each reagent 0.5 and 24 hours after the reagent was prepared by its ability to produce purpurogallin from pyrogallol and hydrogen peroxide. The results are shown below.

| Time (hours) | Reagent with Proteinase K | Reagent without Proteinase K |
|---|---|---|
| 0.5 | 43.9 KU/L | 48.9 KU/L |
| 24 | 47.1 KU/L | 45.3 KU/L |

Proteinase K did not reduce the activity of horseradish peroxidase in the same solution over 24 hours at room temperature.

EXAMPLE 3

A twin reagent for the measurement of glycated protein was prepared and stored at 4° C. The first reagent contained 12 g/L proteinase K, 0.4 g/L peroxidase, 8 mmol/L TOOS, 100 µmol/L potassium ferrocyanide, 300 µmol/L copper acetate and 1.2 mmol/L sodium tartrate in 75 mmol/L EPPS buffer, pH 8.0. The second reagent contained 10000 U/L ketoamine oxidase and 10 mmol/L 4-aminoantipyrene in 83 mmol/L EPPS buffer, pH 8.0.

The reagents were tested with two serum samples using the Cobas Mira as in Example 1 before and after 22 days storage of the liquid reagents at 4° C. The samples were stored frozen in aliquots and a freshly thawed aliquot was used for each analysis. The absorbance changes due to glycated protein in the samples were calculated by subtracting the absorbance just before the addition of the second reagent from the absorbance recorded 2.1 minutes later. The results are shown below.

| Days at | Absorbance change | |
|---|---|---|
| 4° C. | Serum 1 | Serum 2 |
| 0 | 0.0282 | 0.1106 |
| 22 | 0.0310 | 0.1173 |

Therefore, when the complete oxidase/peroxidase assay is performed, there is no decline in the signal due to the degradation of horseradish peroxidase by proteinase K after storage of the reagent at 4° C. for 22 days.

EXAMPLE 4

Three formulations for the measurement of glycated protein were prepared to demonstrate the effect of peroxidase on the ability to remove ascorbate and bilirubin interference. In formulation A, the first reagent contained 12 g/L proteinase K, 0.4 g/L peroxidase and 8 mmol/L TOOS in 75 mmol/L EPPS buffer, pH 8.0. The second reagent contained 10000 U/L ketoamine oxidase and 10 mmol/L 4-aminoantipyrine in 83 mmol/L EPPS buffer, pH 8.0. This formulation contained no ingredients to combat the interferences. Formulation B was the same as A, with the addition of 100 µmol/L potassium ferrocyanide, 300 µmol/L copper acetate and 1.2 mmol/L sodium tartrate to the first reagent. These additions were to reduce interference from bilirubin and ascorbate. Formulation C was the same as B, except that there was no peroxidase in the first reagent. The second reagent contained peroxidase reagent at a concentration of 1.33 g/L. Therefore, after the mixing of sample, reagents and diluents on the analyser according to the protocol of Example 1, all three formulations had the same cuvette concentration of peroxidase.

The three formulations were used to assay for glycated protein in four samples. These were: (1) water, (2) a control serum dilution (one part of water to four parts of serum), (3) serum diluted in the same way with a stock solution of ascorbate such that the concentration of ascorbate in the serum was 400 µmol/L, (4) serum diluted with a stock solution of unconjugated bilirubin such that the concentration of bilirubin in the serum was 400 µmol/L. In the calculation of results with formulation C, the absorbance change seen with the water sample was subtracted from the absorbance changes given by the serum samples to correct for the absorbance due to the peroxidase in the second reagent.

In the Table below, the effects of ascorbate and bilirubin interference are shown as the absorbance change seen with that interference expressed as a percentage of the absorbance change given by the control serum.

| Formulation | Percentage recovery in serum with: | |
|---|---|---|
| | 400 µmol/L ascorbate | 400 µmol/L bilirubin |
| A | 9 | 72 |
| B | 95 | 97 |
| C | 540 | 99 |

Bilirubin at a concentration of 400 µmol/L reduced the absorbance change to 72% of the control sample when used with Formulation A. However, the combination of ferrocyanide, copper and tartrate in the first reagent almost abolished this interference in Formulation B (with peroxidase in the first reagent) and Formulation C (with peroxidase in the second reagent).

Ascorbate interference was particularly severe in Formulation A, with the loss of over 90% of the signal. The additional ingredients of Formulation B reduced this effect to less than 5%. However, when the same amount of peroxidase was added in the second reagent (Formulation C), there was a massive increase in the absorbance change. Therefore, in this system the removal of ascorbate interference depends on the addition of the peroxidase in the first reagent.

EXAMPLE 5

In order to maximise laboratory efficiency, it is desirable that tests should take as little time as possible on an autoanalyser. Indeed, some analysers are incapable of running two reagent chemistries with a first incubation time of greater than three minutes. The detrimental effect of reducing the incubation time of the sample with the first reagent on the ability to remove ascorbate interference is illustrated below with formulation A. Formulation B, however, contains some additional components which significantly improve interference removal.

In formulation A, the first reagent contained 6 g/L proteinase K, 0.4 g/L peroxidase, 8 mmol/L TOOS, 20 µmol/L potassium ferrocyanide, 250 µmol/L copper acetate and 1.0 mmol/L sodium tartrate in 75 mmol/L EPPS buffer, pH 8.0. The second reagent contained 10000 U/L ketoamine oxidase and 10 mmol/L 4-aminoantipyrene in 83 mmol/L EPPS buffer, pH 8.0. This formulation was tested using two different incubation times, 2.9 and 7 minutes.

In formulation B, the first reagent contained 6 g/L proteinase K, 0.4 g/L peroxidase, 8 mmol/L TOOS, 100 µmol/L potassium ferrocyanide, 100 µmol/L copper acetate, 2% w/v cholic acid, 1% w/v polyoxyethylene 10 tridecyl ether and 175 µmol/L bathophenanthroline disulphonic acid in 75 mmol/L EPPS buffer, pH 8.0. The second reagent was the same as in formulation A.

The two formulations were used to assay for glycated protein in three samples, viz: (1) a control serum dilution (by volume, 1 part of water to 4 parts of serum); (2) serum diluted in the same way with a stock solution of ascorbate so that the concentration of ascorbate in the serum was 300 µmol/L; (3) serum diluted with a stock solution of unconjugated bilirubin so that the concentration of bilirubin in the serum was 300 µmol/L.

Sample, reagents and diluents were mixed on the analyser according to the protocol of Example 1, except that the incubation of sample and first reagent was for either 2.9 or 7 minutes.

In the Table below, the effects of ascorbate and bilirubin interferents are shown as the absorbance change seen with that interferent expressed as a percentage of the absorbance change given by the control serum.

| Formulation | 2.9 minute incubation % recovery in serum with: | | 7 minute incubation % recovery in serum with: | |
|---|---|---|---|---|
| | 400 µmol/L ascorbate | 400 µmol/L bilirubin | 400 µmol/L ascorbate | 400 µmol/L bilirubin |
| A | 82 | 87 | 90 | 97 |
| B | 95 | 95 | | |

EXAMPLE 6

A disadvantage of the shorter incubation time of sample and reagent 1, using reagents which overcome the interferences referred to above, is that reaction rates are seen when water is used as the sample. Although this background rate is not apparent when serum is the sample, it is preferable that the method should work with samples other than serum.

In formulation A, the first reagent contained 4 g/L proteinase K, 0.28 g/L peroxidase, 5.6 mmol/L TOOS, 90 µmol/L potassium ferrocyanide, 90 µmol/L copper acetate, 1.8% w/v cholic acid, 1.2% w/v polyoxyethylene 10 tridecyl ether and 144 µmol/L bathophenanthroline disulphonic acid and 5 mmol/L calcium acetate in 75 mmol/L EPPS buffer, pH 8.0. The second reagent contained 13000 U/L ketoamine oxidase and 10.5 mmol/L 4-aminoantipyrene in 50 mmol/L EPPS buffer, pH 8.0.

Formulation B was the same as formulation A, except that 30 mmol/L disodium EDTA was included in the second reagent.

The two formulations were used to assay for glycated protein in three samples, viz: (1) water; (2) serum from a diabetic subject; (3) plasma from a diabetic subject.

The formulations were tested on a Cobas Mira S autoanalyser. The reagent containing the proteinase (250 µL) was mixed in a plastic cuvette with 20 µL of sample and 30 µL of water diluent to wash out the inside of the sample probe. After a 2.9 minute incubation at 37° C., 50 µL of the second reagent and 10 µL of water diluent were mixed into the same cuvette. The cuvette absorbance was measured at 550 nm at 25 second intervals from the start of the procedure until 1.5 minutes after the addition of the second reagent.

Figure 3:
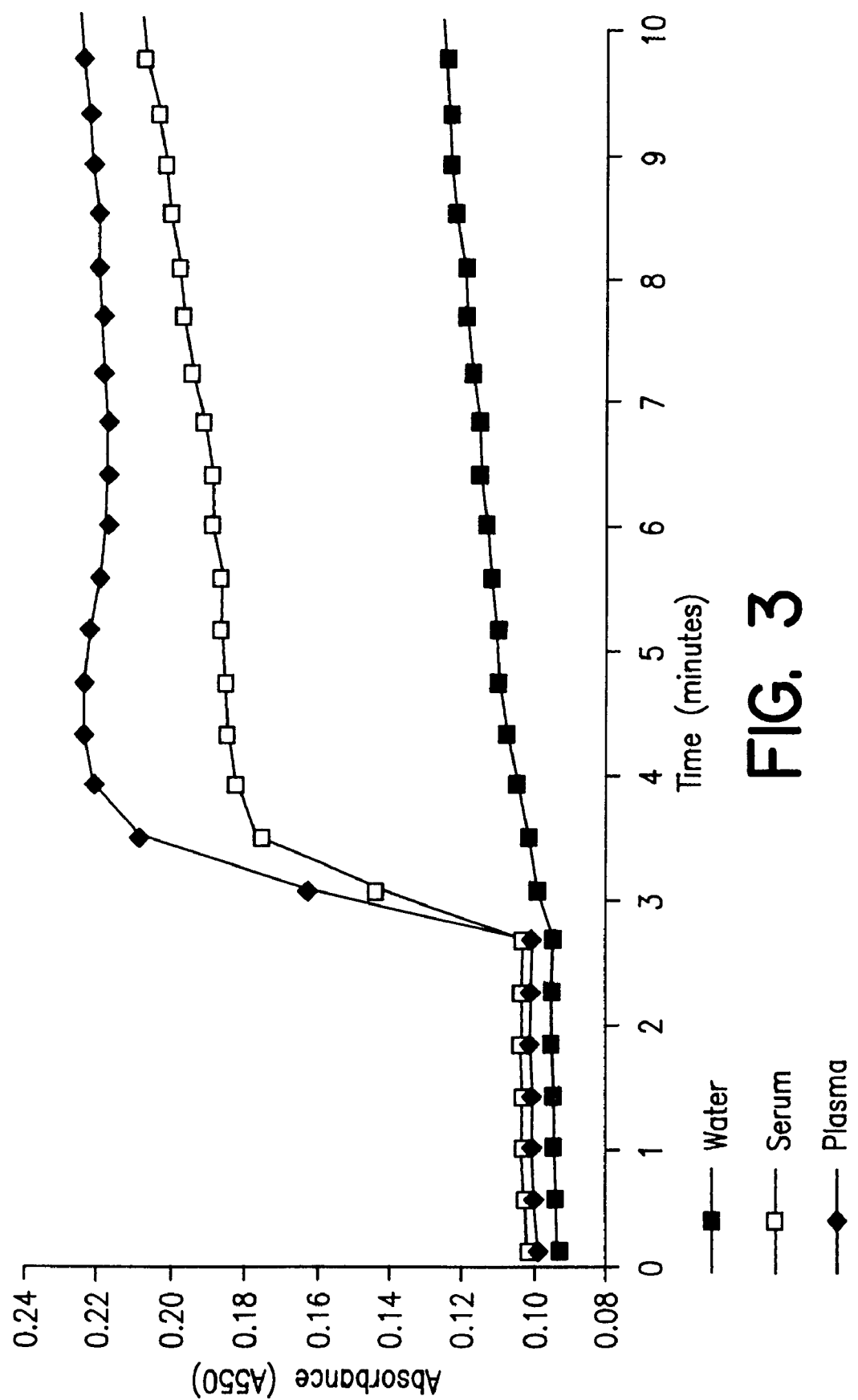
Figure 4:
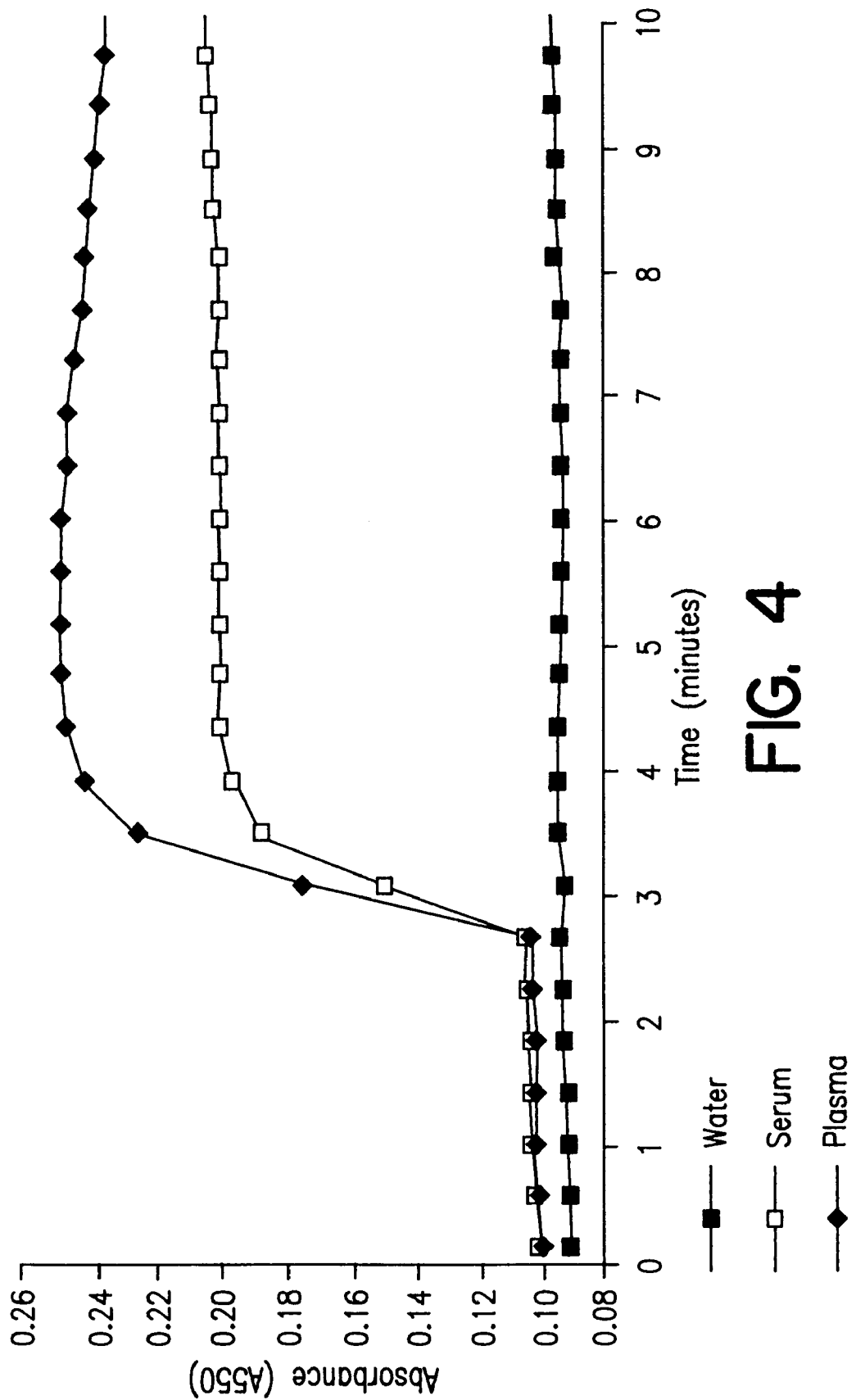

The absorbance profiles seen with formulations A and B are illustrated in accompanying FIGS. 3 and 4, respectively.

It may be seen that the presence of EDTA in the second reagent prevents the increase in absorbance seen after the addition of the second reagent when water is the sample. The signal given by the serum and plasma sample is 15% greater when EDTA is included in the second reagent. Both these effects may be due to the chelation of copper by EDTA. Copper is able to produce a signal with the chromogens and also partially inhibits ketoamine oxidase activity.

EXAMPLE 7

The second reagent may be stabilised by the inclusion of mannitol.

Two formulations of the second reagent were prepared. Formulation A contained 50 mmol/L EPPS buffer, pH 8.0; 10.5 mmol/L aminoantipyrene; 30 mmol/L EDTA and 6000 U/L ketoamine oxidase. Formulation B was the same apart from the inclusion of 5% mannitol. After lyophilisation and reconstitution with demineralised water, each formulation was stored for 21 days both at 25° C. and frozen at −20° C. as a control.

The stability of the reagent formulations with and without mannitol was tested using the Cobas Mira protocol of Example 6 with serum as the sample and a first reagent composed of 3 g/L proteinase K, 0.28 g/L peroxidase, 5.6 mmol/L TOOS, 90 μmol/L potassium ferrocyanide, 90 μmol/L copper acetate, 1.8% cholic acid, 1.2% polyoxyethylene 10 tridecyl ether, 144 μmol/L bathophenanthroline disulphonic acid and 5 mmol/L calcium acetate in 60 mmol/L EPPS buffer, pH 8.0. Results were calculated by subtracting the absorbance of the cuvette at 550 nm just before the addition of the second reagent from the absorbance measured 2.5 minutes after the second reagent addition.

The absorbance changes after 21 days were as follows:

| Storage temperature | Formulation A Abs change | % | Formulation B Abs change | % |
|---|---|---|---|---|
| −20° C. | 0.1036 |    | 0.1062 |    |
| +25° C. | 0.0795 | 77 | 0.1040 | 98 |

Over three weeks at 25° C., the signal produced using Formulation A had fallen to only 77% of the control frozen reagent. However, Formulation B, which contained mannitol, was stable.

EXAMPLE 8

The application of the enzymatic glycated protein method was tested alongside the commercially available nitroblue tetrazolium method (Roche catalogue number 0736694) by comparison with a furosine reference procedure. This involved acid hydrolysis, followed by HPLC quantification of furosine, specific for protein glycation. Fructosyl lysine was used as a standard.

The formulation of the enzymatic reagent was as follows:

The first reagent contained 4 g/L proteinase K, 0.28 g/L peroxidase, 5.6 mmol/L TOOS, 90 μmol/L potassium ferrocyanide, 30 μmol/L copper acetate, 1.8% cholic acid, 0.25% polyoxyethylene-10-tridecyl ether, 144 μmol/L bathophenanthroline disulphonic acid and 5 mmol/L calcium acetate in 60 mmol/L EPPS buffer, pH 8.0. The second reagent contained 10.5 mmol/L aminoantipyrene, 30 mmol/L EDTA, 9000 U/L ketoamine oxidase and 3% mannitol in 50 mmol/L EPPS buffer, pH 8.0.

250 μL of the first reagent was mixed in a plastic cuvette with 20 μL of sample and 30 μL of water diluent to washout the inside of the sample probe. After a 5 minute incubation at 37° C., 50 μL of the second reagent and 10 μL of water diluent were mixed into the same cuvette. The cuvette absorbance was measured at 550 nm at 25 second intervals for a total of 10 minutes. The absorbance change due to glycated protein in the sample was calculated by subtracting the absorbance just before the addition of the second reagent from that measured 5 minutes afterwards.

Figure 5:
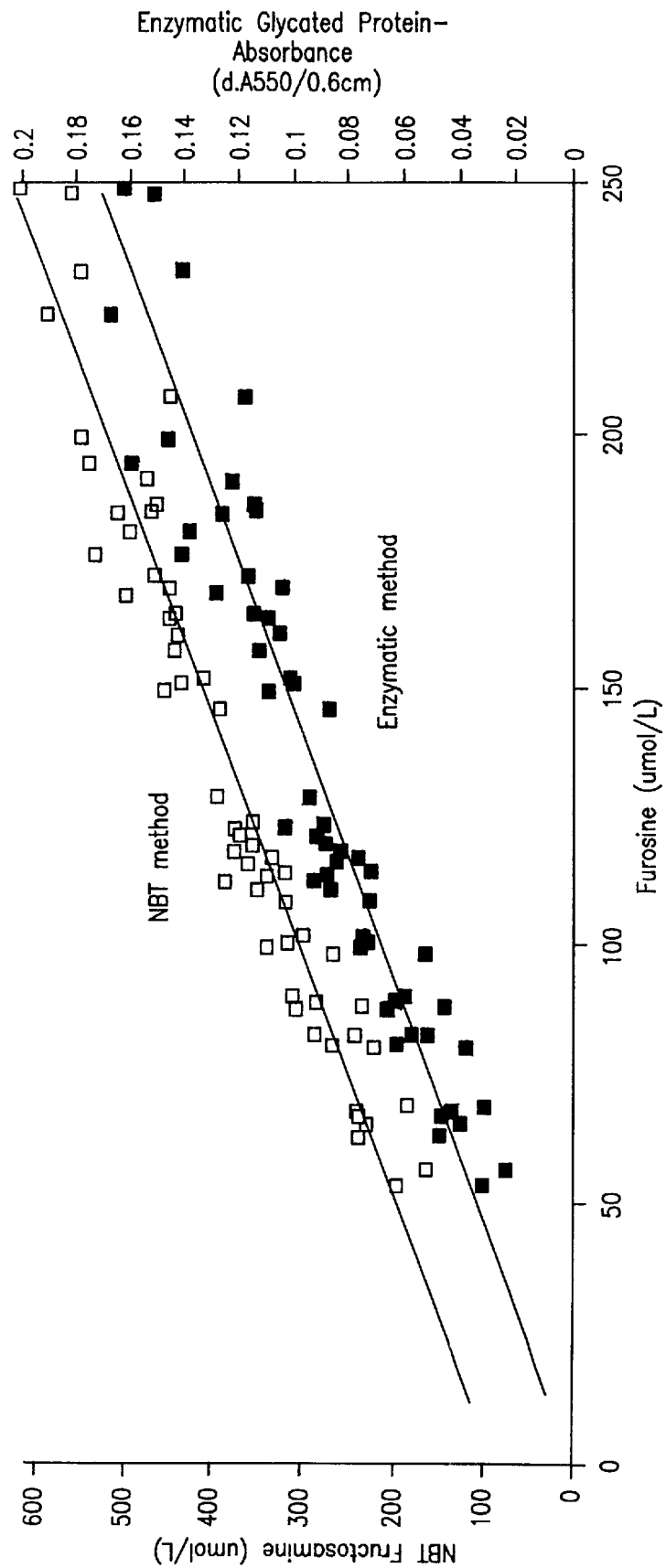

56 serum samples from diabetic subjects were assayed for glycated protein by each of the three methods. Both enzymatic and NBT methods correlated well with the reference method, r=0.95 and 0.96, respectively, (see accompanying FIG. 5). The NBT method showed a positive bias of 95 μmol/L, or 34% of the quoted upper reference limit, while the enzymatic regression line passed very close to the origin. This suggests that both the enzymatic and NBT methods are measuring the same analyte, but that the enzymatic procedure is not subject to a non-specific background reducing activity present in serum.

What is claim is:

1. A method for the determination of a glycated protein in a sample comprising the steps of: a) mixing the sample with a first reagent containing a proteinase and a peroxidase; b) incubating the mixture of step a) for a time sufficient to produce a substrate capable of oxidation by a ketoamine oxidase; c) adding a second reagent containing a ketoamine oxidase to the incubated mixture of step b); and d) measuring hydrogen peroxidase produced or oxygen consumed in step c) to quantify the glycated protein present in the sample.

2. A method as claimed in claim 1 wherein the sample is blood serum or plasma.

3. A method as claimed in claim 1 or claim 2 wherein the proteinase is proteinase K.

4. A method as claimed in any of claim 1 wherein the peroxidase is horseradish peroxidase.

5. A method as claimed in any of claim 1 wherein the ketoamine oxidase is obtainable from the bacterial group Klebsiella, from the fungal genera Fusarium or Acremonium or from the yeast genus Debaryomyces.

6. A method as claimed in any of claim 1 wherein the measurement involves the use of an optionally modified Trinder reaction or an oxygen electrode.

7. A method as claimed in any claim 1 wherein ascorbate interference is countered by the inclusion in the first reagent of a copper (II) compound, a cholic acid or a bathophenanthroline disulphonic acid or a mixture thereof.

8. A method as claimed in any of claim 1 wherein bilirubin interference is countered by the inclusion in the first and/or second reagent of a ferrocyanide salt.

9. A method as claimed in any of claim 1 wherein the second reagent includes ethylene diamine tetraacetic acid and/or mannitol.

10. A kit for the determination of glycated protein comprising: a first reagent containing a proteinase and a peroxidase; a second reagent containing a ketoamine oxidase.

* * * * *